US008187533B2

(12) United States Patent
Elrod

(10) Patent No.: US 8,187,533 B2
(45) Date of Patent: May 29, 2012

(54) DESCENTING SYSTEMS AND METHODS

(75) Inventor: Scott Elrod, Angleton, TX (US)

(73) Assignee: Parah, LLC, Angleton, TX (US)

( * ) Notice: Subject to any disclaimer, the term of this patent is extended or adjusted under 35 U.S.C. 154(b) by 589 days.

(21) Appl. No.: 12/326,240

(22) Filed: Dec. 2, 2008

(65) Prior Publication Data

US 2010/0071633 A1 Mar. 25, 2010

Related U.S. Application Data

(63) Continuation-in-part of application No. 11/714,083, filed on Mar. 5, 2007, now abandoned, which is a continuation-in-part of application No. 11/018,620, filed on Dec. 21, 2004, now Pat. No. 7,939,015.

(51) Int. Cl.
*A61L 9/015* (2006.01)
(52) U.S. Cl. ............ 422/5; 422/120; 422/123; 119/712; 119/905
(58) Field of Classification Search .............. 422/5, 120, 422/123; 119/712, 905
See application file for complete search history.

(56) References Cited

U.S. PATENT DOCUMENTS

| | | | |
|---|---|---|---|
| 1,961,878 A | 6/1934 | Gilkey |
| 2,203,188 A | 6/1940 | Beer |
| 3,214,364 A | 10/1965 | Van Tuyle et al. |
| 3,421,836 A | 1/1969 | Sundin |
| 3,601,292 A | 8/1971 | Bliss |
| 3,670,425 A | 6/1972 | Benjamin |
| 3,750,556 A | 8/1973 | Duke |
| 3,937,967 A | 2/1976 | Steinitz |
| 3,949,056 A | 4/1976 | Nakshbendi |
| 4,045,316 A | 8/1977 | Legan |
| 4,238,857 A | 12/1980 | Waters |
| 4,309,388 A | 1/1982 | Tenney |
| 4,374,571 A | 2/1983 | Hirvela |
| 4,735,010 A | 4/1988 | Grinarml |
| 4,811,159 A | 3/1989 | Foster |
| 4,863,687 A | 9/1989 | Stevens |
| 4,867,052 A | 9/1989 | Cipelletti |
| 4,904,289 A | 2/1990 | Miyakami |
| 4,941,270 A | 7/1990 | Hoffman |
| 4,953,674 A | 9/1990 | Landes |
| 4,990,311 A | 2/1991 | Hirai |
| 5,087,426 A | 2/1992 | Inoue |
| 5,152,077 A | 10/1992 | Liang |
| 5,185,129 A | 2/1993 | Koutrakis et al. |
| 5,192,500 A | 3/1993 | Treddenick |
| 5,303,496 A | 4/1994 | Kowalkowski |
| 5,316,182 A | 5/1994 | Lee et al. |
| 5,342,415 A | 8/1994 | Wasinger et al. |
| 5,383,236 A | 1/1995 | Sesselmann |
| 5,429,271 A | 7/1995 | Porter |
| 5,433,230 A | 7/1995 | Miller |
| 5,433,919 A | 7/1995 | Baltes |
| 5,457,054 A | 10/1995 | Geisinger et al. |
| 5,468,454 A | 11/1995 | Kim |
| 5,484,472 A | 1/1996 | Weinberg |
| 5,514,345 A | 5/1996 | Garbutt |
| 5,520,893 A | 5/1996 | Kasting |
| 5,539,930 A | 7/1996 | Sesselmann |
| 5,547,476 A | 8/1996 | Siklosi |
| 5,667,564 A | 9/1997 | Weinberg |
| 5,681,355 A | 10/1997 | Davis |
| 5,762,648 A | 6/1998 | Yeazell |
| 5,766,560 A | 6/1998 | Cole |
| 5,789,368 A | 8/1998 | You |
| 5,790,987 A | 8/1998 | Sesselmann |
| 5,795,544 A | 8/1998 | Matz |
| 5,829,066 A | 11/1998 | Aibe |
| 5,833,740 A | 11/1998 | Brais |
| 5,835,840 A | 11/1998 | Goswami |
| 5,891,391 A | 4/1999 | Fore |
| 5,911,957 A | 6/1999 | Khatchatrian |
| 5,931,014 A | 8/1999 | Cole |

(Continued)

FOREIGN PATENT DOCUMENTS

EP 0261987 9/1987

(Continued)

OTHER PUBLICATIONS

McElhiney et al., Dec. 2003, Detection of the cyanobacterial hepatoxins microcystins: in Toxicology & Applied Pharmacology, pp. 219-230.

(Continued)

*Primary Examiner* — Sean E Conley
(74) *Attorney, Agent, or Firm* — Holland & Hart

(57) ABSTRACT

Systems and methods for using a scent elimination device to conceal contraband and then training service animals to determine if an ozone-based scent-removal technique has been used to remove scent from contraband are disclosed. The systems and methods comprise providing a plurality of packages. At least one of the plurality of packages containing a predetermined amount of a contraband substance. Further, the systems and methods comprise generating a gaseous stream of descenting material from a portable device. The gaseous stream of descenting material contains ozone. Further, the systems and methods comprise dispersing the gaseous stream of descenting material over the contraband in a concentration sufficient to eliminate the scent. The descented contraband may be placed in an enclosure for transport. Further, the systems and methods comprise introducing a service animal to the plurality of packages. Finally, the systems and methods comprise rewarding the service animal for the successful detection of the at least one of the plurality of packages containing the ozone-based scent remover.

19 Claims, No Drawings

U.S. PATENT DOCUMENTS

| | | |
|---|---|---|
| 5,942,438 A | 8/1999 | Antonoplos et al. |
| 5,983,834 A | 11/1999 | Tai |
| 6,007,770 A | 12/1999 | Peiper |
| 6,009,559 A | 1/2000 | Sesselmann |
| 6,074,608 A | 6/2000 | Matz ........................ 422/83 |
| 6,094,549 A | 7/2000 | Hiraoka |
| 6,134,718 A | 10/2000 | Sesselmann |
| 6,134,806 A | 10/2000 | Dhaemers |
| 6,149,038 A | 11/2000 | Tsai |
| 6,153,111 A | 11/2000 | Conrad |
| 6,156,268 A | 12/2000 | Curry |
| 6,163,098 A | 12/2000 | Taylor |
| 6,182,671 B1 | 2/2001 | Taylor et al. |
| 6,218,189 B1 | 4/2001 | Antonoplos et al. |
| 6,267,242 B1 | 7/2001 | Nagata et al. |
| 6,284,204 B1 | 9/2001 | Cole |
| 6,312,507 B1 | 11/2001 | Taylor |
| 6,336,964 B1 | 1/2002 | Omatsu et al. |
| 6,340,447 B2 | 1/2002 | Johnson |
| 6,340,497 B2 | 1/2002 | Wilson |
| 6,355,216 B1 | 3/2002 | Kristiansson |
| 6,368,867 B1 | 4/2002 | Gibson et al. |
| 6,379,435 B1 | 4/2002 | Fukunaga |
| 6,503,547 B1 | 1/2003 | Lima |
| 6,564,591 B2 | 5/2003 | Noyes |
| 6,565,805 B2 | 5/2003 | Khatchatrian |
| 6,576,190 B1 | 6/2003 | Park |
| 6,613,277 B1 | 9/2003 | Monagan |
| 6,630,105 B1 | 10/2003 | O'Neill et al. |
| 6,632,407 B1 | 10/2003 | Lau |
| 6,635,439 B2 | 10/2003 | Morrison et al. |
| D486,357 S | 2/2004 | Leba |
| 6,790,411 B1 | 9/2004 | Read |
| 6,896,853 B2 | 5/2005 | Lau |
| 6,967,008 B1 | 11/2005 | Barnes |
| 7,117,687 B2 | 10/2006 | Naaman |
| 7,118,608 B2 | 10/2006 | Lovell |
| 2002/0030022 A1 | 3/2002 | Bradley |
| 2002/0071795 A1 | 6/2002 | Jensen |
| 2002/0094298 A1 | 7/2002 | Monagan |
| 2003/0044308 A1 | 3/2003 | Toth |
| 2003/0066767 A1 | 4/2003 | Felsenthal |
| 2003/0089010 A1 | 5/2003 | Wechter et al. |
| 2003/0108460 A1 | 6/2003 | Andreev et al. |
| 2003/0111435 A1 | 6/2003 | Chen |
| 2004/0002349 A1 | 1/2004 | Yamagishi et al. ........ 455/456.3 |
| 2004/0047775 A1 | 3/2004 | Lau et al. |
| 2004/0096354 A1 | 5/2004 | Normura et al. |
| 2004/0149329 A1 | 8/2004 | Hess |
| 2004/0163184 A1 | 8/2004 | Waldron et al. |
| 2004/0221396 A1 | 11/2004 | Johnson |
| 2005/0186108 A1 | 8/2005 | Fields |
| 2005/0207951 A1 | 9/2005 | Lee et al. ................. 422/186.07 |
| 2006/0006122 A1 | 1/2006 | Burns et al. |
| 2006/0096331 A1 | 5/2006 | Kim |
| 2006/0151896 A1 | 7/2006 | Wang |
| 2007/0092414 A1 | 4/2007 | Malyon |
| 2007/0166186 A1* | 7/2007 | Stec .................... 422/5 |
| 2007/0212253 A1 | 9/2007 | Elrod |
| 2008/0036594 A1 | 2/2008 | Kates ..................... 340/541 |
| 2009/0038555 A1 | 2/2009 | Reese |
| 2009/0139459 A1 | 6/2009 | Habacivch et al. |
| 2010/0107991 A1 | 5/2010 | Elrod |
| 2010/0289655 A1 | 11/2010 | Elrod et al. |

FOREIGN PATENT DOCUMENTS

| | | |
|---|---|---|
| JP | 1100948 A | 6/1997 |
| JP | 11009949 A | 6/1997 |
| JP | 11226106 A | 2/1998 |
| JP | 11226108 A | 2/1998 |
| JP | 2003001/237 A2 | 6/2001 |
| WO | WO0151096 | 1/2001 |
| WO | WO03089017 | 4/2003 |
| WO | 2004067043 | 8/2004 |
| WO | WO2005077425 | 2/2005 |
| WO | WO2005021135 | 3/2005 |

OTHER PUBLICATIONS

Fehrenbacher, J., Robotic Pollution-Sniffing ECO Dogs, 2 Pages, Feb. 26, 2007.

* cited by examiner

DESCENTING SYSTEMS AND METHODS

CROSS-REFERENCE TO RELATED APPLICATIONS

The Present Invention is a Continuation-in-Part of U.S. patent application Ser. No. 11/714,083, filed on 5 Mar. 2007. In turn, U.S. patent application Ser. No. 11/714,083 is a Continuation-in-Part of U.S. patent application Ser. No. 11/018,620, filed on 21 Dec. 2004. The Present Invention and the aforementioned U.S. patent applications are co-owned, and incorporated fully herein for all purposes. The Present Invention claims priority to the aforementioned U.S. patent applications under the Patent Laws of the United States of America.

BACKGROUND OF THE PRESENT INVENTION

1. Field of the Present Invention

The Present Invention is directed generally to descenting systems and methods. More particularly, the Present Invention is directed to systems and methods for reducing or eliminating the various odors of contraband through the use of ozone-based descenting products. Additionally, the Present Invention is directed to systems and methods for the training and detection, by service animals, of the use of such systems and methods for reducing or eliminating the various odors of contraband through the use of ozone-based descenting products.

2. Description of the Related Art

There is currently known a variety of descenting systems and methods, examples of which may be found in U.S. Pat. Nos. 4,309,388; 4,867,052; 4,941,270; 5,087,426; 5,433,919; 5,468,454; 5,484,472; 5,514,345; 5,539,930; 5,547,476; 5,667,564; 5,681,355; 5,762,648; 5,766,560; 5,789,368; 5,790,987; 5,911,957; 5,931,014; 6,007,770; 6,009,559; 6,134,806; 6,134,718; 6,149,038; 6,156,268; 6,163,098; 6,284,204; 6,312,507; 6,355,216; 6,379,435; 6,503,547; 6,564,591; 6,565,805; and 6,576,190, and U.S. patent application Ser. No. 09/941,510 (which has been published as U.S. Publication No. 2003/004308), and the references cited therein. The disclosures of each of these citations are incorporated herein in their entireties.

The aforementioned citations relate generally to descenting systems and methods. In addition to this aspect, detection of the use of a descenting system and method is also important. For example, service animals, such as narcotic-sniffing canines, have been employed to discern whether individuals are importing contraband into a geographic location. Typically, this determination is done by taking advantage of the inherent acuteness of the canine olfactory sense. The importation of such contraband is, obviously, illegal. Nevertheless, in an effort to profit on the "black market," importers (or, more appropriately, smugglers) have taken many steps in an attempt to circumvent the canine olfactory sense. One option has been to mask, or cover up, the odor of the contraband with substances such as coffee grounds. Alternatively, descenting systems and methods, such as that described herein, may be employed. For example, descenting systems may be placed within the presence of the contraband in an effort to reduce or eliminate the odor emanating from such contraband enough to reduce or eliminate the success rate of service animals.

It has further been discovered that gaseous ozone effectively kills bacteria and substantially reduces or eliminates odors. The advantages of ozone over other known masking and descenting methods are numerous, and take advantage of the facts that ozone is a gas that (1) can eliminate odors emanating from an object; (2) can eliminate odors in a space; (3) is completely natural to the environment; and (4) leaves behind a very pleasant clean smell. Known ozone generators include electrical discharge and ultraviolet light. Further, known ozone generators may be operated with either AC or DC current sources.

Additionally, ozone is well known to treat odorous air, microorganisms, bacteria, mold, smoke, aromatic hydrocarbons and various organic compounds. See, for example, U.S. Pat. Nos. 1,961,878; 2,203,188; 3,421,836; 3,750,556; 3,937,967; 3,949,056; 4,045,316; 4,863,687; 4,904,289; 4,990,311; 5,087,426; 5,835,840; 5,983,834; 6,094,549; 6,613,277; and 6,632,407, U.S. patent application Ser. Nos. 09/445,012 (which has been published as U.S. Publication No. 2002/0030022) and 10/983,215 (which has been published as U.S. Publication No. 2006/0096331), and foreign references EP 0261987; WO 200151096; WO 2003089017; WO 2005021135; and WO 2005077425, and the references cited therein, each of which teaches the use of ozone to descent various items. The disclosures of each of these citations are incorporated herein in their entireties.

Generally, the items to be descented are placed in a container, a portable enclosure or a special descenting closet or room, at which time the descenting system operates to descent the particular items. However, as soon as the particular items leave the container, enclosure, closet or room, the odor resumes emanation from the items. Thus, any prior descenting, using the disclosed methods, is of little value.

Ozone has been used for, inter alia, decontaminating buildings and for decolorizing denim garments. U.S. Pat. No. 5,833,740 (the disclosure of which is incorporated herein in its entirety) discloses an apparatus for sterilizing bottles utilizing ozone. This citation recognizes that ozone in large quantities can be harmful or irritating.

Ozone is also a powerful oxidizing agent. Ozone has 150% of the oxidizing potential of chlorine and twice the oxidizing potential of bromine. Ozone has been shown to be much more effective than chlorine with a reaction time up to 10 times faster. Ozone also readily self-destructs into simple diatomic oxygen due to its inherent instability. Ozone oxidizes biological products and kills bacteria.

Catalytic ionization of air using ultraviolet light is known to produce a mixture of ozone-containing hydroxyl and hydroperoxide ions. Ionization devices which are used to eliminate smoke and odors are known in the art to produce hydroxyl and hydroperoxide ions, e.g., those used in automobiles.

Thus, the need exists to develop an effective descenting system which overcomes the disadvantages set forth herein. Additionally, the need exists to develop a training mechanism for service animals and their handlers to detect the use of such descenting systems.

BRIEF SUMMARY OF THE INVENTION

The Present Invention is directed generally to descenting systems and methods. More particularly, the Present Invention is directed to systems and methods for reducing or eliminating the various odors of contraband through the use of ozone-based descenting products. Additionally, the Present Invention is directed to systems and methods for the training and detection, by service animals and their handlers, of the use of such systems and methods for reducing or eliminating the various odors of contraband through the use of ozone-based descenting products.

What follows are some of, but not all, the objects of the Present Invention. In addition to the specific objects stated below for at least certain preferred embodiments of the Present Invention, there are other objects and purposes which will be readily apparent to one of skill in this art who has the benefit of the Present Invention's teachings and disclosures. It is, therefore, an object of at least certain preferred embodiments of the Present Invention to provide:

New, useful, unique, efficient, nonobvious methods and systems for substantially reducing or eliminating the scent of contraband; and New useful, unique, efficient, nonobvious systems and methods for teaching service animals and their handlers to detect the use of such systems and methods on contraband.

Other objects and advantages of the Present Invention will become apparent from the description of the preferred embodiments and the claims. Accordingly, characteristics and advantages of the Present Invention described herein, and additional features and benefits, will be readily apparent to those skilled in the art upon consideration of the following detailed description of preferred embodiments.

The embodiments of the Present Invention described herein are not limited to any particular individual feature, but include combinations distinguished from the prior art in their structures, functions and/or results achieved. Features of the Present Invention have been broadly described so that the detailed descriptions that follow may be better understood, and in order that the contributions of the Present Invention to the arts may be better appreciated. There are, of course, additional aspects of the Present Invention described below and which may be included in the subject matter of the claims to the Present Invention. Those skilled in the art who have the benefit of the Present Invention, its teachings and suggestions will appreciate that the conceptions of this disclosure may be used as a creative basis for designing other structures, methods and systems for carrying out and practicing the Present Invention. The claims of the Present Invention are to be read to include any equivalent devices or methods which do not depart from the spirit and scope of the Present Invention.

The Present Invention recognizes and addresses the previously-mentioned problems and long-felt needs and provides a solution to those problems and a satisfactory meeting of those needs in its various possible embodiments and equivalents thereof. To one of skill in this art who has the benefits of the Present Invention's realizations, teachings, disclosures and suggestions, other purposes and advantages will be appreciated from the following description of certain preferred embodiments, given for the purpose of disclosure, when taken in conjunction with the accompanying drawings. The detail in these descriptions is not intended to thwart the Present Invention's object to claim the Present Invention no matter how others may later disguise it by variations in form, changes or additions of further improvements.

The Abstract that is part hereof is to enable the U.S. Patent and Trademark Office and the public generally, and scientists, engineers, researchers and practitioners in the art who are not familiar with patent terms or legal terms of phraseology, to determine quickly from a cursory inspection or review the nature and general area of the disclosure of the Present Invention. The Abstract is neither intended to define the Present Invention, which is done by the claims, nor is it intended to be limiting of the scope of the Present Invention in any way.

It will be understood that the various embodiments of the Present Invention may include one, some, or all of the disclosed, described and/or enumerated improvements and/or technical advantages and/or elements in the Claims of the Present Invention.

DETAILED DESCRIPTION OF THE INVENTION

For purposes of the Present Invention, the following terms used herein are defined or augmented as follows:

"Person" includes what is traditionally known as a "hunter," that is, a person who hunts animals, including wild game and other animals, in their natural habitats. "Person" also includes nature enthusiasts, trappers, military personnel (including those seeking to evade others and/or avoid capture), hikers, fishers, backpackers and photographers.

"Hunt" or "hunting" is the searching of wild game and other animals for the purposes of encountering, attracting, avoiding, escaping from, photographing, avoiding detection by, capturing, killing and/or observing such wild game and other animals.

"Handler" is a police officer, narcotics officer, game warden, customs officer, animal trainer, civilian and the like, that uses a service animal to detect contraband.

"Service animal" is any animal, such as a human, dog, cat, bird, pig, fish and the like, that is capable of being trained to detect contraband.

"Animal" includes any small or large game animal such as dogs, cats, deer, elk, sheep, pig, moose, caribou, bird, rabbit, elephant, mountain lions, bear and fish, and combinations thereof. Additionally, "animal" may include human beings. For example, a human may desire to prevent the detection of human body odors or odors resulting from the illegal transportation of humans.

"Contraband" is any substance that is illegal to possess or transport, but maintains a black market, such as marijuana, cocaine, heroin, amphetamines, apples, oranges, pineapples, bananas, explosives, plastiques, gun powder, exotic birds, reptiles, fish, mammals, humans and paper currency (both genuine and counterfeit).

"Descenting material generators" include generators that produce a material as a gas, a fine mist, a spray with solids or some combination thereof that is capable of descenting or masking contraband. The materials include oxidants, ozone, hydroxyl radicals, hydroperoxides and other known descenting materials; with or without an operating integrated fan. A "mist" produced by an ozonator or descenting material generator is a mist of descenting material and a liquid, e.g., water or organic-solvent material (e.g., alcohols like methanol or ethanol or isopropanol or glycol ether, e.g., ethylene glycol methyl ether and ethylene glycol dimethylether) capable of solubilizing descenting material.

Descenting material generators of all sizes, weights, power sources and types are widely available from various sources, such as Ozonics, Sharper Image, Biozone Scientific, Ozone Solutions and Air Zone. Optionally, descenting material generators may contain an additional ion generator source for negative ionization of the air. Catalytic ionization of air using ultraviolet light is known to produce a mixture of ozone-containing hydroxyl and hydroperoxide ions. These type of units are also commercially available, e.g., the IONIC BREEZE products from Sharper Image.

Optionally, descenting material generators may of the type that includes atomized water or hydrogen peroxide to produce highly reactive hydroxyl radicals. Such generators are disclosed, e.g., in Japanese patent references JP11-00948A; JP11-009949A; JP2003001/237A2; JP11-226108A; and JP 11-226106A. The disclosures of each of these Japanese citations are incorporated herein in their entireties. Further, descenting material generators may include the simultaneous or intermittent generation of other known oxidizing agents, bacteria and odor removing substances such as chlorine, zinc ricinoleate and/or cyclodextrine, e.g., as contained in FEBREEZE fabric softener.

It is preferable that the descenting material generators be light weight and portable, and powered by battery means, solar means hand crank means (for instances in which one carries small amounts of contraband on one's person or in a small container or suitcase) or other generating means. When the contraband is in a larger container, such as building, a room, truck container or automobile, or when larger amounts of contraband are involved, it is preferable to have the same features. Nevertheless, even when large amounts of contraband are involved, it is still preferable to use the smallest, low weight generators possible that will effectively descent the contraband, as these may be better hidden from visual detection. However, generators weighing up to about 8 lbs. and more may still be used.

In general, light-weight descenting material generators can produce lower levels of ozone and generate ozone for a shorter period of time, especially when small batteries are used. However, many battery-operated portable descenting material generators can last eight hours and more on one battery charge. The ozone generation source can be of any type, including ultraviolet light, electrical discharge or a combination of both. Certain portable, battery-operated and solar-operated ozone generators have ultraviolet light sources as the ozone generation source due mainly to the lower voltage required for ultraviolet light. Small, portable battery and solar operated descenting material generators are available which have small fans, though many have no fan at all.

Larger descenting material generators capable of operating on AC current can also generate ozone through ultraviolet light, electrical discharge or a combination of both. Electrical discharge descenting material generators can be capable of generating large amounts of ozone in a smaller size container. However, the addition of blowers, fans and transformers, while within the scope of the Present Invention, can result in some descenting material generators being heavier than other descenting material generators having ultraviolet light sources.

One advantage of including at least a small fan is that the ozone can be dispersed over a large area more readily. However, it is not necessary that a fan be included in the descenting material generator. For example, when ozonating a larger area like a truck container, especially if the container is full of contraband, or contains a smaller amount of contraband hidden within a larger amount of legal cargo, an ozone generator having a fan or fan blower is preferred, but not required. If a fan or fan blower is used, a fan can be used which makes minimum noise, especially beyond about a ten foot radius of fan operation so as not to be audibly detected by a human, handler or service animal.

Certain descenting material generators are capable of producing approximately 15-5000 mg of ozone and more, per hour. For safety consideration, it is desired that the contraband is exposed to a constant concentration of 0.1 ppm of ozone or less in such a concentration over an 8 hour time period or less, especially when the contraband is a human or animal, however, exposures of contraband to larger concentrations, e.g., up to 0.2 ppm ozone and more, may be desirable to effectively mask contraband having high odors, such as marijuana and fruits. A preferred descenting material generator is one which can maintain about 0.1 ppm or less total ambient concentration of ozone over an area of approximately a six foot radius of the contraband.

In certain aspects, the Present Invention provides for a method for reducing contraband scent in a space between the contraband and the service animal, the methods including generating descenting material with a material descenting generator, introducing the descenting material into a space between a human being and the service animal, the space containing foreign scent (i.e., odor emanating from the contraband), and reducing the foreign scent in the space with the descenting material. In certain embodiments, the descenting material is ozone and the method further includes exposing the contraband to a time-weighted average value of 0.1 ppm of ozone in ambient air or less over an area within a radius of six feet of the contraband; exposing the contraband to a time-weighted value of 0.2 ppm or ozone in ambient air or less; or exposing the contraband over a time period of eight hours or less to a time-weighted value of 0.1 ppm of ozone in ambient air or less.

In other aspects, the Present Invention provides for a method for reducing foreign scent in a space between contraband and the service animal, the methods including producing descenting material with a material descenting generator with directional apparatus, directing said descenting material in a desired direction into the space, the directional apparatus including at least one director in communication with the generator for receiving produced descenting material from the generator and for directing said descenting material into the space, and reducing the foreign scent (i.e., the odor emanating from the contraband) in the space with the descenting material. In certain embodiments, the descenting material is ozone and the method further includes exposing the contraband to a time-weighted average value of 0.1 ppm of ozone in ambient air or less over an area within a radius of six feet of the contraband; exposing the contraband to a time-weighted value of 0.2 ppm or ozone in ambient air or less; or exposing the contraband over a time period of eight hours or less to a time-weighted value of 0.1 ppm of ozone in ambient air or less.

For humans that are avoiding an encounter with a service animal for a leisure manner, e.g., those attempting to conceal only small amounts of contraband past a handler or law enforcement officer, a small battery-powered descenting material generator, such as the Biozone Scientific Model 50 Personal Air Purifier, may be used. For persons attempting to conceal contraband for an extended period, e.g., an hour or more, a larger ozone generator, such as the Biozone Scientific TRAVELAIRE, the OMZ-200 from Ozone Solutions or the HR-100 from Ozonics, may be used. For those engaging in concealing larger amounts of contraband, a descenting material generator such as the HR-100 may be used. Alternatively, the Ozone Solutions Model MZ-450 or OMZ-3400 may be used. The MZ-450 and OMZ-3400 are primarily suited for 110 V AC operation, but can alternatively be operated with for four or more hours on a single battery charge. For even higher amounts of ozone output, descenting material generators currently sold by EcoQuest International, which also sells generators of hydroxyl and hydroperoxide ions, may be preferred.

As battery technology improves, it may be possible to operate high ozone concentration descenting material generators with batteries that weigh much less. The use of ozone can quickly reduce or eliminate odors (including human odors), volatiles and contaminates (all collectively referred to as "foreign scents") on a person, the person's clothing or equipment and in the space between the person and a service animal or handler.

Without being bound by any theory, it is believed that in one aspect, ozone in the air kills bacteria in certain body areas of humans, including in the underarm and groin areas—areas responsible for producing many of the odor-causing volatiles emitted by humans. In another aspect, volatile odors produced and emitted directly by humans via the skin, mouth or feet are oxidized by ozone into compounds that are much less volatile and therefore far less detectable to service animals. In another aspect, it is believed that ozone in the air substantially reacts with volatiles in the air emitted by the contraband so that the scent is below the level of detection by the service animal. In yet another aspect, it is believed that the more powerful (but much shorter life-time) hydroxyl and/or hydroperoxide radical oxidants, produced by ozone reacting with ultraviolet rays and/or moisture in the air, contribute to odor elimination.

Without being bound by theory, it is believed that in one aspect, ozone reacts with the residue or exposed surface of the contraband to produce an oxidized substance that has no odor or that is no longer volatile and therefore not detectable by the service animal or human. In another aspect, any volatile odors that are produced and emitted directly by the contraband are reacted with the gaseous ozone to produce an oxidized substance that has no odor or that is no longer volatile and therefore not detectable by the service animal or human. In another aspect, it is believed that ozone in the air kills the bacteria in the underarm and groin area that is responsible for producing many of the odor-causing volatiles emitted by human and animal contraband. In another aspect, any volatile odors that are produced and emitted directly by human or animal contraband via the skin are oxidized by the ozone into compounds that are much less volatile and therefore far less detectable to humans and service animals. In another aspect, any volatile odors that are produced and emitted directly by human contraband via the feet and escape through the shoe or socks are oxidized by the ozone into compounds that are much less volatile and therefore far less detectable to humans and service animals. In yet another aspect, any pheromone or combinations of pheromones (which contain a wide variety of alcohol, ester, and saturated organic functionality) that are produced and emitted by human and animal contraband at levels far to small to be detectable by humans but not by service animals, are oxidized by the ozone into compounds that are much less volatile and therefore far less detectable to service animals. In yet another aspect, odorants in breath of human and animal contraband such as aldehydes, alcohols and acids are oxidized by the ozone into compounds that are much less volatile and therefore far less detectable to humans and service animals. In yet another aspect, it is possible that oxidized volatiles of contraband, even if they are still somewhat volatile and detected by humans and service animals, are changed enough in composition that the human or service animal no longer detects the oxidized volatiles as human or animal contraband. In yet another aspect, it is possible that higher levels of ozone in the environment around the contraband overpowers any odor volatiles such that the service animal or human perceives the higher concentration of ozone as the result of commonly-occurring and natural lightening.

There is no limitation to the number of ozone generators used except for taking the precaution of not allowing human or animal contraband to come into contact with an unsafe amount of ozone that adversely affects human health. For cost and convenience, one ozone generator located on, in or near the contraband is sufficient. Multiple generators located on, in or near the contraband, and combinations thereof, may result in better concealment of the contraband from the law enforcement officer or service animal.

In accordance with another embodiment of the Present Invention, the human scent of a military person desiring to escape detection by other humans or service animals (e.g., dogs) is reduced or eliminated enough to avoid detection. More particularly, there is provided a method for reducing or eliminating human or any other foreign scent from clothing, e.g., clothing and equipment used by military persons desiring to evade capture—through the use of ozone or hydroxyl and hydroperoxide ions produced by ionization in a manner that would not cause irritation or injury to the user or equipment.

The oxidizing gas may be used alone or diluted with air as when packaged in a compressed gas form. Ozone which is produced by generators in amounts up to 8000 mg/hr or more can be compressed or diluted with an inert gas and compressed into small containers.

It will be appreciated by persons skilled in the art that numerous variations and/or modifications may be made to the Present Invention without departing from the spirit or scope of the Present Invention as broadly claimed.

The following Examples further illustrate the Present Invention, but are not intended to be limiting thereof. Examples I, II and III demonstrate how ozone can be used to hide the presence of a human to an animal, while Example IIII demonstrates how ozone was used with narcotics to conceal contraband from service animals.

EXAMPLES

Example I

A hunter placed himself in a cedar bush located in the Fort Peck Wilderness Area in Montana. A Biozone Scientific Model 50 was placed on a backpack located between the hunter's legs and turned on. An elk was observed approaching within 8 yards of the hunter about 45 minutes after the ozonator was turned. The elk passed downwind and through the hunter's scent line without detecting the hunter.

Example II

A hunter placed himself in a home-made blind of native brush in South Texas along with an Ozonics HR-100 hung from the blind and located about 10 inches behind and above his head. The hunter did not use any specialized clothing, masks or scents prior to or during the hunt, but was camouflaged. Deer corn was placed at the perimeter of the blind going out to about 30 feet from the blind. Within 10 minutes of turning on the HR-100 to its maximum setting, up to 6 white tail deer at a time and several birds (cardinals and finch) were observed feeding within 10 yards downwind of the hunter in a 3 hour time span. One young buck was observed within 5 feet downwind of the blind where the hunter was laying. None of the deer, cardinals or finch appeared to have scented the hunter.

Example III

A person climbed a tree in the woods near his house and turned on an Ozonics HR-100. A neighbor's dog walked by some time later. When directly downwind the dog stopped, sniffed, looked confused, but walked on. When he came to where the person had walked into the woods he stopped and sniffed the person's trail for a few feet then left and continued on his way. The dog did not detect that the person was in the tree.

Example IIII

A narcotics test was performed using 4 different police trained dog handlers and their trained narcotics dogs. Latex gloves were placed on the hands of anyone handling the narcotics, cardboard boxes and Ozonics HR-100s used in this demonstration so that the trained dogs would not be influenced by the scent of a human.

In a room was placed 5 legal sized cardboard boxes spaced approximately 2 to 3 feet apart from one another. In a random order was placed 1 small bag of cocaine wrapped in plastic into a box. Into another box was placed a small bag of heroin wrapped in plastic that contained an HR-100 that was turned on. Into another box was placed just an HR-100. Two boxes had nothing in them. After putting lids on each box and then 10 minutes of running the HR-100s, one police officer and their dog at any given time entered the room. The police officer instructed their dog to search each of the boxes. All the dogs identified the box containing the cocaine almost immediately by scratching the box and then laying down in front of the box. The dogs were immediately rewarded by their handler by opening the box to show the plastic wrapped cocaine and giving praises to their dogs. It took several attempts for the 4 dogs to detect the heroin masked by the ozone, and all had to be instructed by their handlers to put their noise into the carrying holes of the cardboard box to detect the heroin. None of the dogs reacted to the box containing just the HR-100.

It will now be appreciated by anyone skilled in the art that ozone can unexpectedly be used to conceal contraband from service animals having been trained to detect small amounts of odor from contraband that humans cannot generally detect.

In a newly-discovered use for the system and method of the Present Invention, the descenting system described herein can be used to train contraband-detecting service animals to determine if a system, such as the Present Invention, has been used in an attempt to eliminate the scent of the contraband.

Unfortunately, contraband is routinely smuggled into sovereigns in which it is illegal to possess, such as the United States. Consequently, law enforcement personnel have a vested interest in breaking the smuggling procedure. Taking advantage of the innate acuteness of service animals such as contraband-sniffing canines, law enforcement personnel have routinely used such canines on the front line of defense against the smugglers. However, the smugglers have been known to use a wide variety of substances and devices to mask the odor associated with the narcotic contraband, including coffee grounds. Once enforcement personnel were alerted to the smugglers use of coffee grounds to mask narcotics, the narcotics personnel then trained their dogs to detect the use of coffee grounds as a mask for the narcotics. The new use for the Present Invention provides law enforcement personnel with an added level of defense in their struggle against the contraband smugglers attempting to use ozone based descenters to eliminate or reduce the odor of contraband.

For the new use, a plurality of packages are provided, wherein at least one package contains a predetermined amount of contraband. Preferably, the amount of contraband is enough to be detected by the contraband-detecting canines. Further, an ozone-based scent remover, similar to that described herein with regard to the Present Invention, is placed in or near at least one of the packages, and operated to remove the odor emanating from the contraband. Additionally, "dummy" packages—packages containing nothing— may be disposed in the area as well. Optionally, at least one package can contain just an ozone-based scent remover.

A service animal, such as a contraband-detecting canine, is then introduced to the area in which the packages are located. In time, and relying on the superior olfactory sense of the animal, the service animal will be able to detect which package(s) contain contraband, which package(s) contain contraband masked by the ozone-based scent remover, which package(s) contains just an ozonator, and which package(s) contain nothing. Training of the contraband-detecting canine to detect the various packages is preferably done according to known training techniques. To assist in the training of the service animal, rewards are typically provided, in the form of food and/or praise, to the animal for a successful detection.

To further aid in the successful detection of a person attempting to use an ozone-based descenting system to conceal contraband, the handler may optionally posssses an ozone detection device to confirm the presence of ozone above the normal ambient concentration of ozone. The ozone detection device may be any that are well known in the art such as a badge, test strip, gas detector (such as that available from UV Process Supply) or sensor (such as that available from Ecosensor). In this way, the handler can confirm for example, that the concentration of ozone is elevated in one particular area compared to an area just a short distance away from the area of interest. This may provide the handler with the evidence needed to obtain a search warrant to investigate further. Alternatively, if the smuggler is present, the handler could show the result to the smuggler and request that the smuggler turn off any ozone-based descenting device so that the service animal can then positively detect any contraband.

The Present Invention, therefore, provides in certain, but not necessarily all embodiments, a system and method for reducing or eliminating the various odors that are detectable by service animals, and to the detection, by those animals, of such systems and methods.

In conclusion, therefore, it is seen that the Present Invention and the embodiments disclosed herein and those covered by the appended Claims are well adapted to carry out the objectives and obtain the ends set forth. Certain changes can be made in the subject matter without departing from the spirit and the scope of the Present Invention. It is realized that changes are possible within the scope of the Present Invention and it is further intended that each element or step recited in any of the following Claims is to be understood as referring to the step literally and/or to all equivalent elements or steps. The following Claims are intended to cover the Present Invention as broadly as legally possible in whatever form it may be utilized. The Present Invention claimed herein is new and novel in accordance with 35 USC §102 and satisfies the conditions for patentability in §102. The Present Invention claimed herein is not obvious in accordance with 35 USC §103 and satisfies the conditions for patentability in §103. This Specification and the Claims that follow are in accordance with all of the requirements of 35 USC §112. The Inventor may rely on the Doctrine of Equivalents to determine and assess the scope of his Invention and of the Claims that follow as they may pertain to apparatus not materially departing from, but outside of, the literal scope of the Present Invention as set forth in the following Claims. All patents and applications identified herein are incorporated fully herein for all purposes.

What is claimed is:

1. A method for using a scent elimination device to conceal contraband for the training of service animals, the method comprising:
   generating a gaseous stream of descenting material, wherein the gaseous stream of descenting material contains ozone;
   dispersing the gaseous stream of descenting material over a first contraband item in a concentration sufficient to eliminate the scent;
   providing a second contraband item untreated with the gaseous stream of descenting material;

introducing a service animal to the first and second contraband items;

rewarding the service animal for the successful detection of the second contraband item using the service animal's olfactory senses.

2. The method of claim 1, wherein the ozone further comprises at least one of hydroxy radicals, hydroperoxides and oxidants.

3. The method of claim 1, wherein the first and second contraband items comprise at least one of marijuana, cocaine, heroin, amphetamines, apples, oranges, pineapples, bananas, explosives, plastiques, gun powder, exotic birds, reptiles, fish, mammals, humans, paper currency and combinations thereof.

4. The method of claim 1, further comprising dispersing the gaseous stream of descenting material over the first contraband item, in a concentration sufficient to eliminate the scent from humans.

5. The method of claim 1, further comprising dispersing the gaseous stream of descenting material over the first contraband item, in a concentration sufficient to eliminate the scent from the service animal.

6. The method of claim 5, wherein the service animal is at least one of german shepherd, beagle, golden retriever, great pyrenees, labrador and poodle.

7. The method of claim 1, wherein the scent elimination device is portable.

8. A method for training service animals to determine if an ozone-based scent-removal technique has been used to remove scent from contraband, the method comprising:

providing a plurality of packages, at least one of the plurality of packages containing a predetermined amount of a contraband substance;

disposing an ozone-based scent remover in or near at least one of the plurality of packages;

dispersing a gaseous stream of descanting material generated by the ozone-based scent remover over the contraband in a concentration sufficient to eliminate the scent;

introducing a service animal to the plurality of packages;

rewarding the service animal for the successful detection of the at least one of the plurality of packages containing the ozone-based scent remover using the service animal's olfactory senses.

9. The method of claim 8, wherein the ozone-based scent remover further comprises at least one of hydroxy radicals, hydroperoxides and oxidants.

10. The method of claim 8, wherein the contraband comprises at least one of marijuana, cocaine, heroin, amphetamines, apples, oranges, pineapples, bananas, explosives, plastiques, gun powder, exotic birds, reptiles, fish, mammals, humans, paper currency and combinations thereof.

11. The method of claim 8, further comprising: disposing an ozone-based scent remover in or near at least one of the plurality of packages; and dispersing the gaseous stream of descenting material over the contraband in a concentration sufficient to eliminate the scent from humans.

12. The method of claim 8, further comprising: disposing an ozone-based scent remover in or near at least one of the plurality of packages; and dispersing the gaseous stream of descenting material over the contraband in a concentration sufficient to eliminate the scent from service animals.

13. The method of claim 12, wherein the service animal is at least one of german shepherd, beagle, golden retriever, great pyrenees, labrador and poodle.

14. A method for using a scent elimination device to conceal contraband and then training service animals to determine if an ozone-based scent-removal technique has been used to remove scent from contraband, the method comprising:

providing a plurality of packages, at least one of the plurality of packages containing a predetermined amount of a contraband substance;

generating a gaseous stream of descenting material, wherein the gaseous stream of descenting material contains ozone;

dispersing the gaseous stream of descenting material over the contraband, in a concentration sufficient to eliminate the scent, wherein the descented contraband may be placed in an enclosure for transport;

introducing a service animal to the plurality of packages;

rewarding the service animal for the successful detection of the at least one of the plurality of packages containing the descenting material using the service animal's olfactory senses.

15. A method of using a service animal to detect when an ozone-based descenting device is being used to conceal contraband, comprising:

introducing the service animal to a package;

having the service animal detect the presence of contraband and ozone using the service animal's olfactory senses and provide an indication that the contraband is present in the presence of ozone;

confirming the presence of contraband;

rewarding the service animal.

16. The method of claim 15, further comprising a handler confirming the presence of ozone by using an ozone detection device.

17. The method of claim 16, wherein the ozone detection device is in the form of a badge, test strip, gas detector or sensor.

18. The method of claim 1, further comprising rewarding the service animal for the successful detection of the descenting material.

19. The method of claim 1, further comprising rewarding the service animal for the successful detection of the first contraband item masked with the descenting material.

* * * * *